(12) United States Patent
Kessler

(10) Patent No.: US 7,204,827 B2
(45) Date of Patent: Apr. 17, 2007

(54) SECUREMENT DEVICE FOR INDWELLING CATHETERS OR INTRODUCERS

(75) Inventor: Alan Kessler, Los Angeles, CA (US)

(73) Assignee: Maddoc Medical Products, Inc., Los Angeles, CA (US)

(*) Notice: Subject to any disclaimer, the term of this patent is extended or adjusted under 35 U.S.C. 154(b) by 65 days.

(21) Appl. No.: 10/789,892

(22) Filed: Feb. 26, 2004

(65) Prior Publication Data
US 2005/0192540 A1 Sep. 1, 2005

(51) Int. Cl.
*A61M 5/32* (2006.01)

(52) U.S. Cl. .......... 604/180; 128/DIG. 6; 128/DIG. 26

(58) Field of Classification Search ............... 604/174, 604/177, 179, 180, 344, 345; 606/232; 128/DIG. 6, 128/DIG. 26
See application file for complete search history.

(56) References Cited

U.S. PATENT DOCUMENTS

| | | | |
|---|---|---|---|
| 4,778,446 A | | 10/1988 | Jensen |
| 4,966,590 A | * | 10/1990 | Kalt .......................... 604/180 |
| 5,147,322 A | * | 9/1992 | Bowen et al. ............... 604/180 |
| 5,224,935 A | * | 7/1993 | Hollands ..................... 604/180 |
| 5,282,463 A | * | 2/1994 | Hammersley .......... 128/207.15 |
| 5,314,411 A | | 5/1994 | Bierman et al. |
| 5,637,098 A | | 6/1997 | Bierman |
| 5,643,216 A | * | 7/1997 | White ......................... 604/174 |
| D393,903 S | | 4/1998 | Bierman |
| 5,792,115 A | * | 8/1998 | Horn ........................... 604/174 |
| 5,855,591 A | * | 1/1999 | Bierman ...................... 606/232 |
| 6,117,163 A | | 9/2000 | Bierman |
| 6,213,979 B1 | | 4/2001 | Bierman |
| 6,582,403 B1 | | 6/2003 | Bierman et al. |

OTHER PUBLICATIONS

International Search Report for Application No. PCT/US05/05333, completed Dec. 1, 2005.

* cited by examiner

*Primary Examiner*—Nicholas Lucchesi
*Assistant Examiner*—Theodore J. Stigell
(74) *Attorney, Agent, or Firm*—Knobbe Martens Olson & Bear, LLP

(57) ABSTRACT

A securement device for Indwelling Catheters or Introducers having a pad with an adhesive backing for securement to the skin of a patient. A base is mounted on the pad having one or more spaced holes therethrough with an elongated strand extending through said hole or holes. The strand may be wrapped around or passed through a connector mounted on the base and the free end(s) thereof may be tied to the strand or to another strand arising from the base.

43 Claims, 6 Drawing Sheets

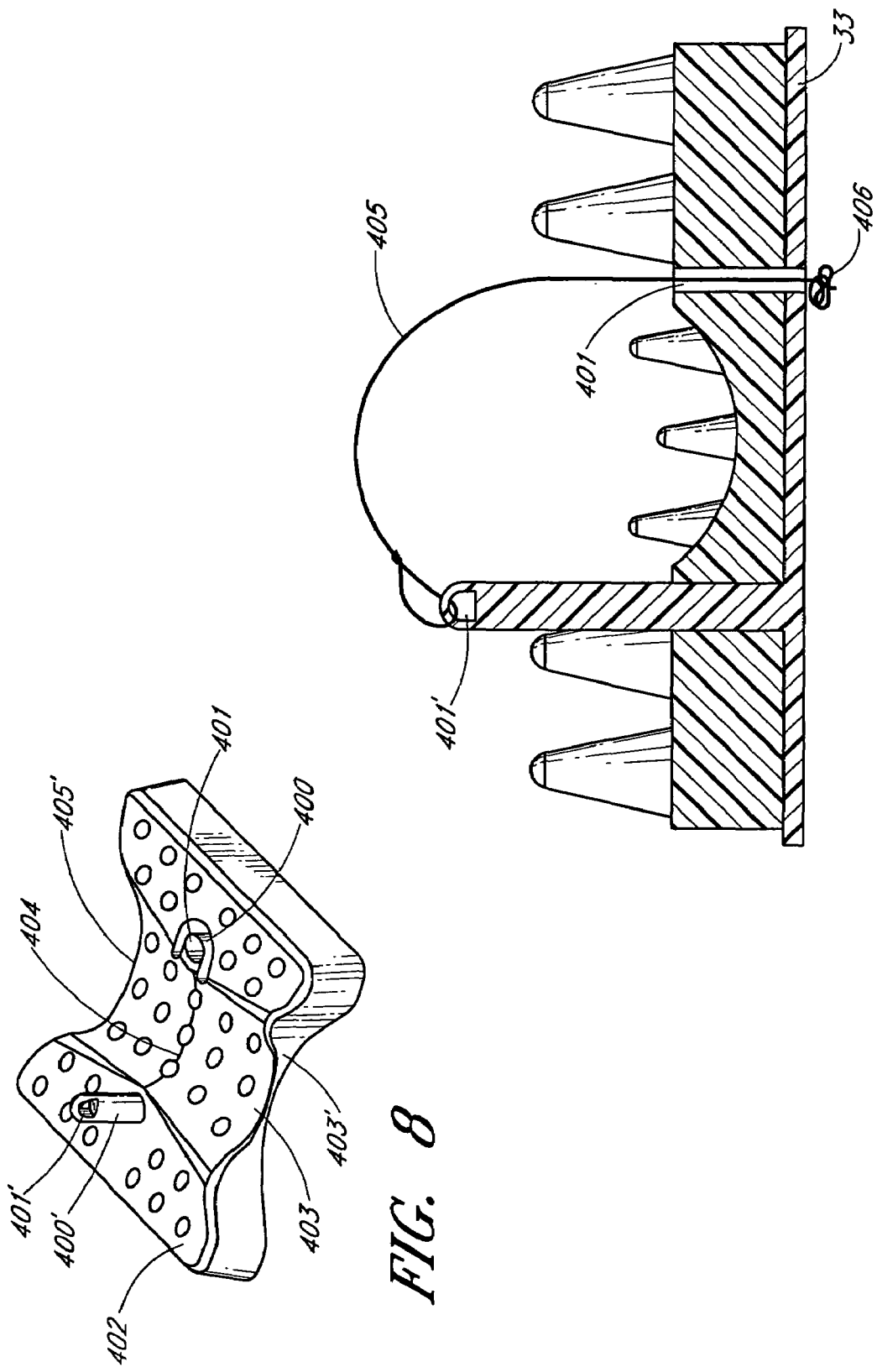

SECUREMENT DEVICE FOR INDWELLING CATHETERS OR INTRODUCERS

BACKGROUND OF THE INVENTION

1. Field of the Invention

The invention relates to securement devices; and, more particularly, to anchoring systems for anchoring or securing medical articles to the body of a patient.

2. Related Art

It is well known in the treatment of patients to introduce fluids and medications directly into the bloodstream. Many devices are known for quickly and easily securing a catheter, tube, etc. to the skin of a patient without suturing.

Various devices have been suggested in the past which require carefully machining of parts of said medical articles to form apertured ears or tabs to anchor the securement strands to a catheter or the like. Certain securement devices require specially manufactured strands or posts with protuberances. Other securement devices are specifically adapted to a particular type of catheter or the like thus not easily accommodating catheters of different configurations.

These devices do not put tension on the strands holding the catheter in place.

There is a need for a securement device for percutaneous sheath introducers and other medical devices which uses flexible strands for securement means thus allowing versatility and flexibility and does not require careful and expensive machining of the medical articles to be secured. Such a device should easily accommodate catheters of varying configurations.

SUMMARY OF THE INVENTION

It is an object of this invention to provide a securement device for indwelling catheters or introducers and other medical articles which uses strands of material as the securement means of tying a catheter or the like in position on the body of a patient.

It is another object of this invention to provide such a device having a base secured to a pad adapted to be secured to the body of a patient, the base holding a catheter or the like in a firm fixed position on the base.

It is still another object of this invention to carry out the foregoing objects placing tension on the strands holding a catheter or the like in place on the base.

These and other objects are preferably accomplished by providing a pad having an adhesive backing for securement to the skin of a patient. A base is mounted on the pad having a one or more holes therethrough with an elongated strand(s) extending down through said hole or holes. The strand may be wrapped around a connector mounted on the base and tied to itself or two or more such strands, the free ends thereof tied to secure the connector to the base.

BRIEF DESCRIPTION OF THE DRAWINGS

FIG. 8 is a view similar to FIG. 5 showing still another modification of the base of FIG. 1; and FIG. 9 is a side view, in section, of the base of FIG. 8.

DESCRIPTION OF THE PREFERRED EMBODIMENT

Figure 1:
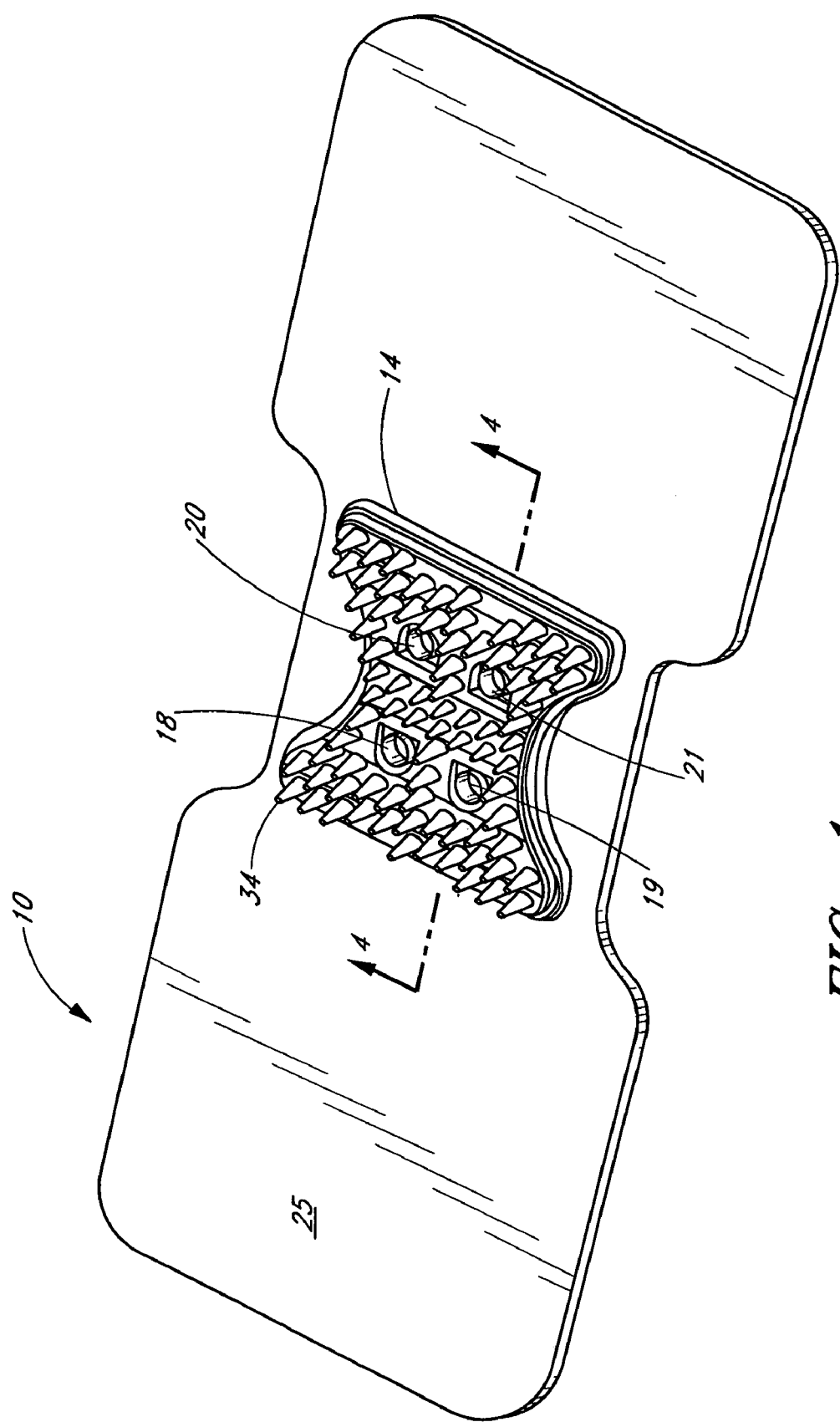
FIG. 1 is a perspective view of a securement device in accordance with the teachings of the invention.
Figure 2:
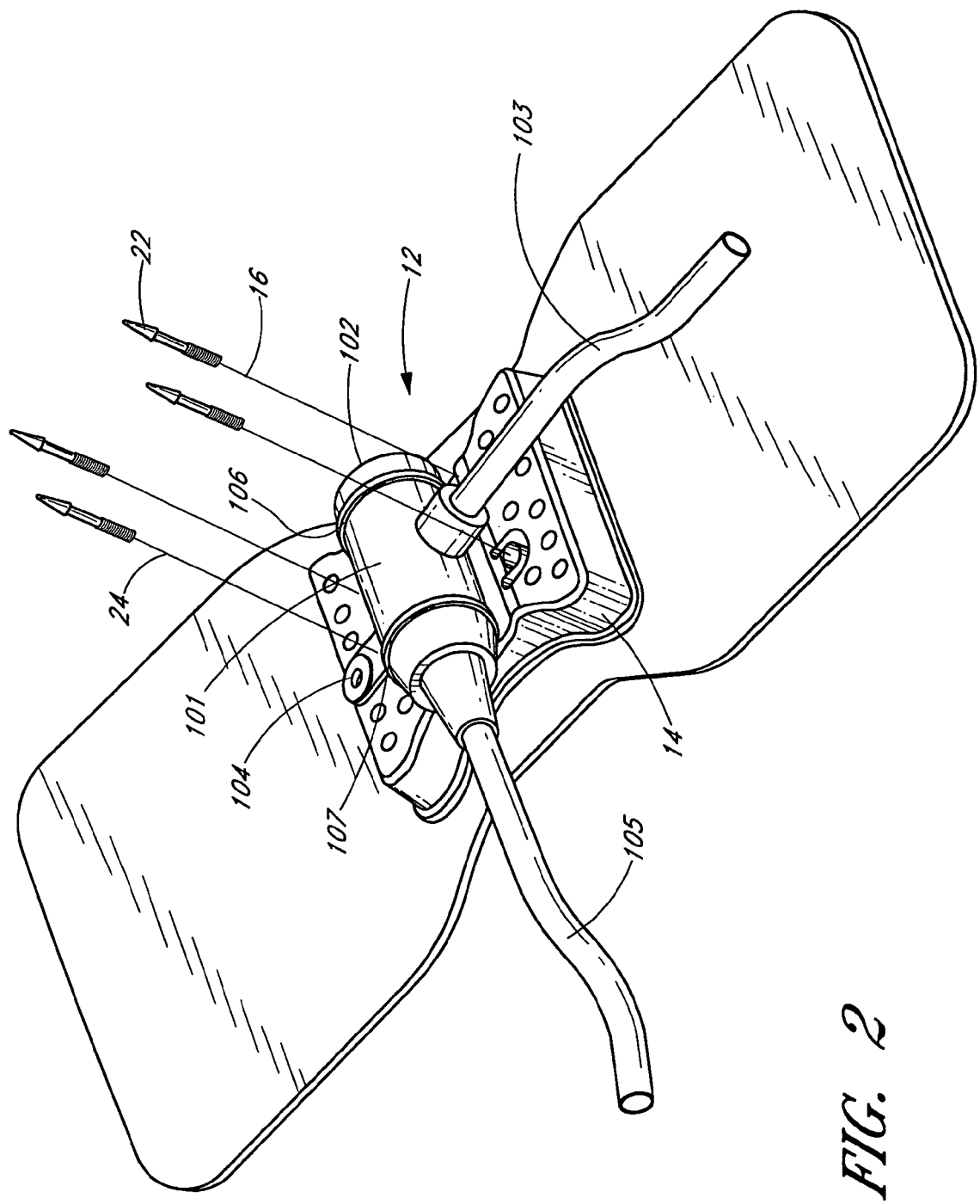
FIG. 2 is a perspective view of the device of FIG. 1 showing a connector mounted thereto.

Referring now to FIG. 1, a securement device 10 is shown adapted to be used in connection with a catheter type conventional fluid line connector 12 (FIG. 2). It is to be understood that, although illustrated as to be used with a catheter, the securement device 10 herein can be used with other types of medical devices or articles such as, for example, CVCs, PICCs, Foley catheters, hemodialyses catheters, surgical drainage tubes, feeding tubes, chest tubes, nasogastric tubes, or with wires or cables coupled to external or implanted electronic devices or sensors. Thus, as used herein, "medical devices or articles" means generally any suitable or generic type catheter, fluid supply and drainage line, connector, adaptor, electrical wire or cable, etc. which may be retained by the securement device herein and used to introduce fluids or allow drainage or the like through medical devices into or out of the patient's body.

Figure 3:
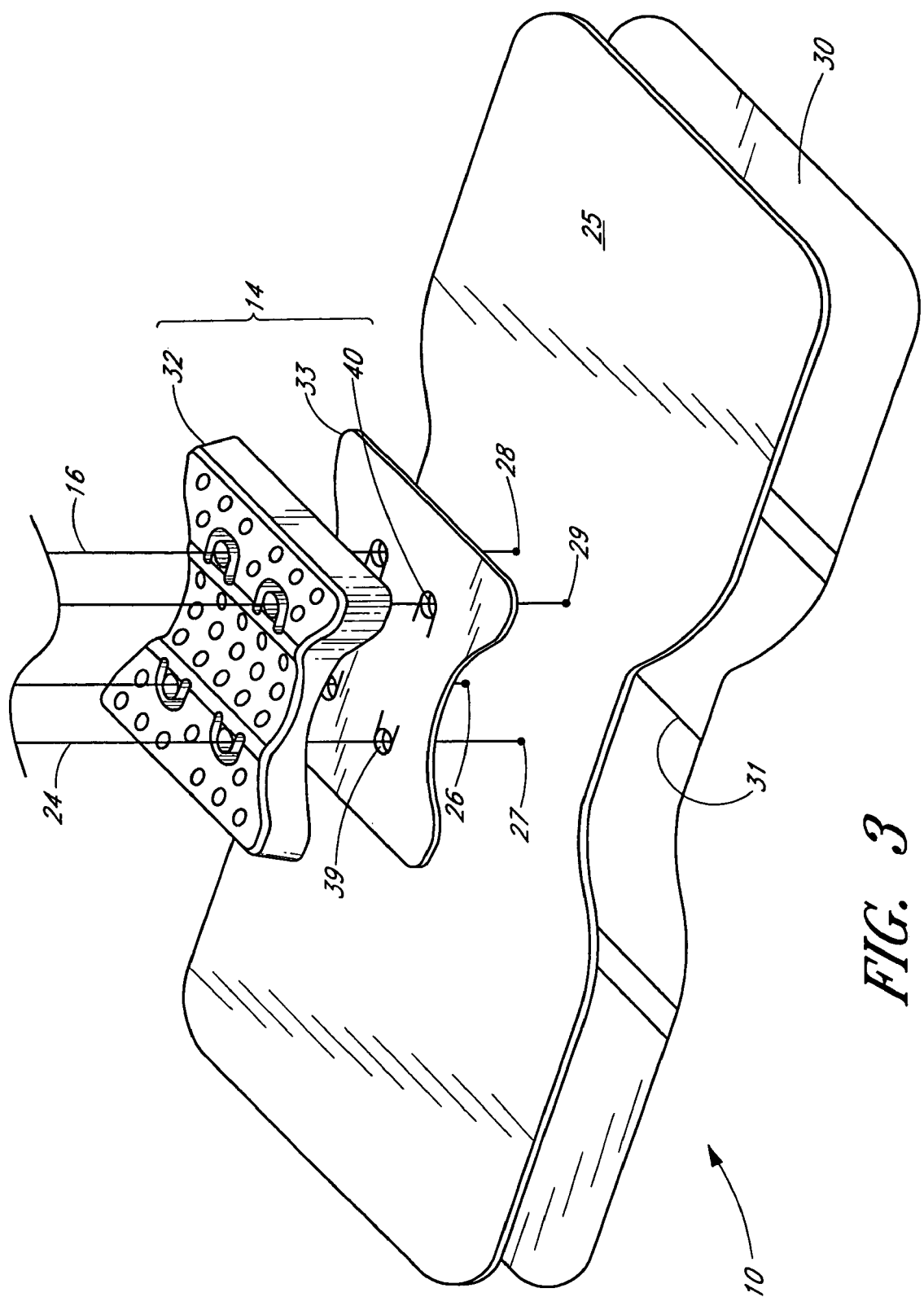
FIG. 3 is an exploded view of the base, pad and backing of the device of FIGS. 1 and 2 illustrating a pair of flexible strands extending through aligned holes in the base and pad.

Securement device 10 thus includes a base 14 adapted to be secured to an anchor pad 25 (FIG. 3) and one or more filaments or strands, such as 2 strands 16, 24 (FIGS. 2 and 3) that extend from base 14.

Base 14 is secured to anchor pad 25 which is configured as shown (generally referred to as a butterfly configuration) and secured thereto in any suitable manner, such as by a solvent bond adhesive.

One or more holes 26 through 29 (FIG. 3) are provided through pad 25 aligned with holes 18 to 21 (FIG. 1), respectively, in base 14.

In the example shown, two such strands 16, 24 are shown adapted to be fed through holes 18 through 21 (FIG. 1) in base 14 and aligned holes 26 to 29 in pad 25. Thus, one strand 16 may be fed alone through aligned holes 19, 27 and up through aligned holes 29, 21 and the other strand may extend down through aligned holes 18, 26 and up through aligned holes 28, 20. Of course, any suitable number of strands and holes may be used.

Each strand 16, 24 may have a pointed distal end 22 (FIG. 2) which may be hardened, such as a lacquered tip. Any suitable strand length may be used depending on the application.

The anchor pad 25 may be of flexible material as is well known in the art and may comprise a layer of a closed cell, low-density polyethylene foam and a bottom layer of a medical grade adhesive. A removable paper or plastic backing 30 (see FIGS. 3 and 4), conforming to anchor pad 25, covers the bottom adhesive surface of pad 25 before use. The backing 30 is of a suitable material to resist tearing and may be divided into a plurality of pieces, such as 2, for ease in attachment of pad 25 to the patient's skin. Preferably, backing 30 is of 2 pieces, adhesively attached to the bottom of pad 25 at its center 31 (FIG. 3) having end portions unattached to pad 25 which can be pulled apart to expose one half of the adhesive pad at a time. Other means may be used, such as a single piece of backing which has a portion extending beyond the edge of pad 25 to ease removal as is well known in the art.

Base 14 is comprised of two parts (FIG. 3), an upper support base 32 secured to a lower part or support plate 33 which in turn is secured to pad 25. Plate 33 is preferably of a polycarbonate material glued or otherwise secured to pad 25.

Support base 32 may be of a suitable molded polymeric material having an upper surface covering with a plurality of upstanding generally conically shaped protrusions 34 (FIG. 4) extending upwardly therefrom.

A spring beam 35 is mounted internally or integrated into support plate 33 for reasons to be discussed.

Holes 18 through 21 in support base 32 are aligned with like holes (FIG. 3) through support plate 33 which holes are also aligned with holes 26 to 29, as previously discussed.

Figure 4:
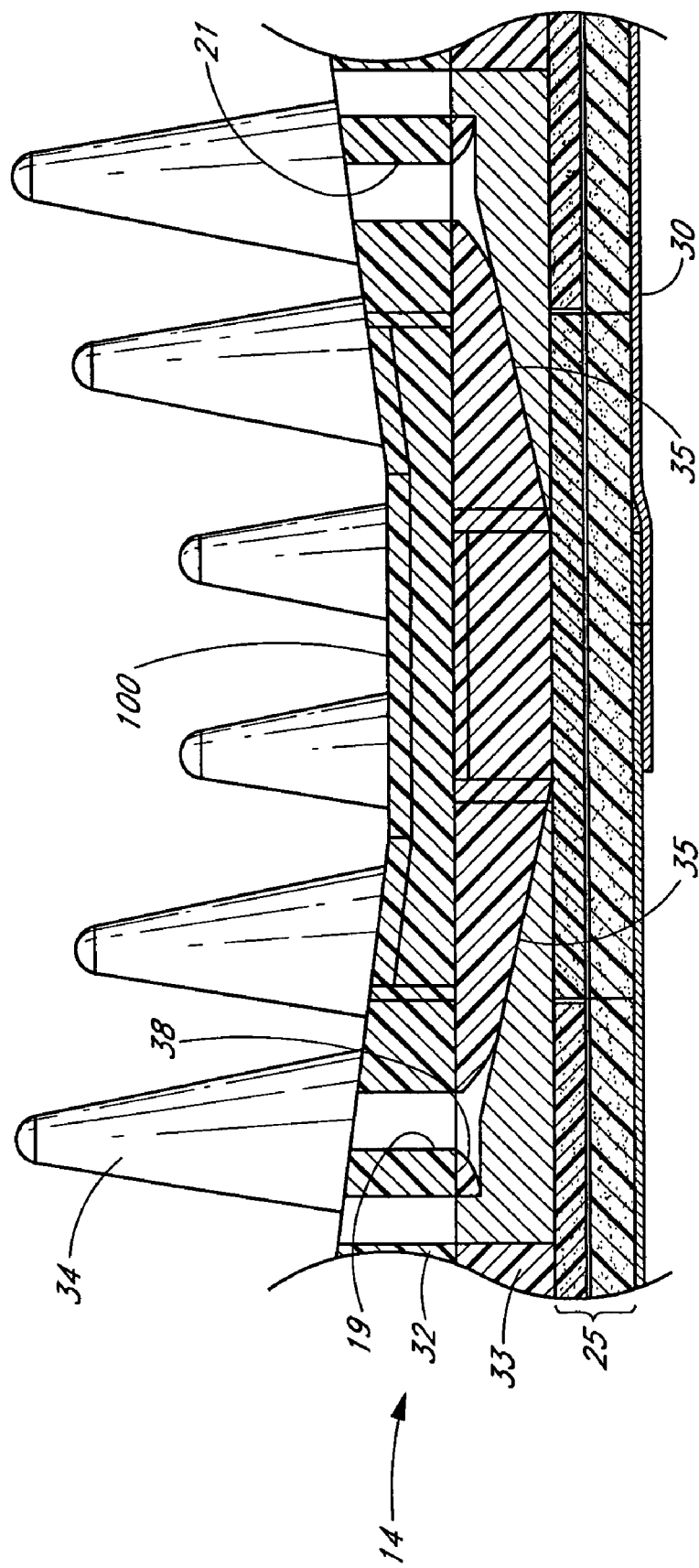
FIG. 4 is a side view, in section, illustrating the interior structure of the base device of FIGS. 1 to 3.

As seen in FIG. 4, holes 18 to 21 are circular through the beam 35. The edges of each hole are radiused (see radiused wall portion 38—FIG. 4).

As seen in FIG. 4, the protrusions 34 may vary in overall height and are preferably of a suitable elastomeric material. Strands 16, 24 may be of any suitable material, such as silk. Silk is less likely to slide during use. Thus, strand 24 extends through hole 19 in upper support base 32, down through aligned hole 39 in support plate 33, about the underside of spring beam 35 (which thus provides tension when strand 24 is tied), up through hole 40 in support plate 33, and through aligned hole 21 in upper support base 32 and upwardly as shown. Alternatively, all strands could extend up and be knotted at the respective holes 19, 21 or glued to the underside of the support plate 33.

As discussed, any suitable materials may be used, such as a fabric material for pad 25 with a base 14 of polycarbonate or similar material glued to pad 25. The radiused edges 38 of the holes eliminate sharp cutting edges. Strands or sutures 16, 24 may be No. 1 braided silk sutures. Support base 32 may be of any suitable polymeric material, such as a material of about 35 A Durometer.

As seen in FIG. 4, upper support base 32 is slightly concave at its middle 100.

Looking at FIG. 2, the connector 12 has a main hub portion 101 having an inlet port 102 at one end for insertion of a catheter (not shown) therein and an elongated tubular portion 103 extending therefrom for fluid instillation. Hub portion 101 also has an apertured ear 104 on one side of the hub portion 101 and a flexible inlet tube 105 fluidly coupled to hub portion 101 for introducing fluids and directing an inserted catheter or wire therein, as is well known in the art. Of course, any suitable connector or catheter configuration may be used.

As seen in FIG. 2, connector 12 rests in the middle or concave portion 100 of upper support base 32. The protrusions 34 assist in holding the connector 12 in position. The strands 16, 24 extend through the aligned holes in upper support base 32 and lower support plate 33 and under beams 35.

Connector 12 may have one or more spaced annular grooves, such as grooves 106, 107 (FIG. 2). Strands 16, 24 may be tied to connector 12 in any suitable manner. For example, strand 16 may first be extended through the hole in apertured ear 104, then wrapped around groove 106 and the free ends tied. Strand 24 may be wrapped around groove 107 and the free ends tied. The overall length of one side of each strand may be easily adjusted to accommodate tying.

Although a particular type of connector is disclosed, having annular grooves, obviously any suitable type of connector may be used as long as strands 16, 24 can be wrapped around or through the holes and tied. The hardened ends 22 allow easy insertion through the aligned holes and the apertured ear.

The concave center 100 of upper support base 32 acts as an anti-roll channel for connector 12. This also prevents folding of the base 32 in the center.

Although 2 strands 16, 24 may be used to tie connector 12 to base 32, obviously one may be used. Thus, at least one strand is sufficient utilizing the teachings of the invention.

Figure 5:
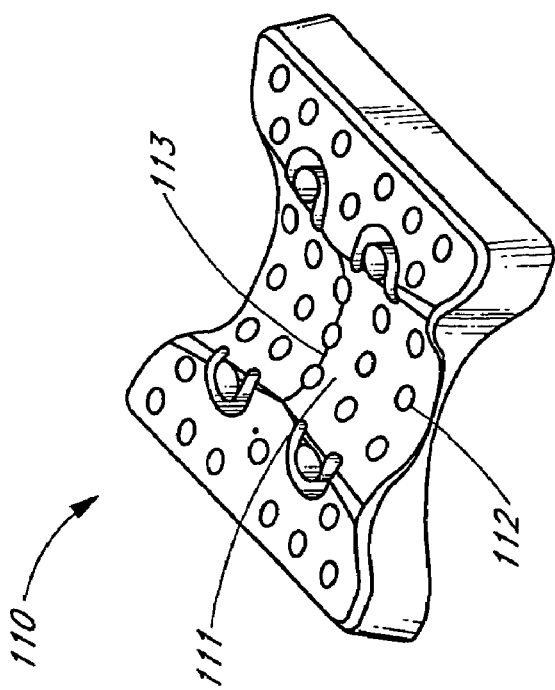

In a further embodiment of the invention, wherein like numerals refer to like parts of FIGS. 1 to 4, as seen in FIG. 5, base 110 otherwise identical to base 14, may have the upper surface 111 of upper support base 112 slightly raised, at its center 113, so that when connector 12 is secured in position, the inlet port 102 is in a slightly elevated position for easy insertion of a catheter into a connector mounted thereon (not shown).

Figure 6:
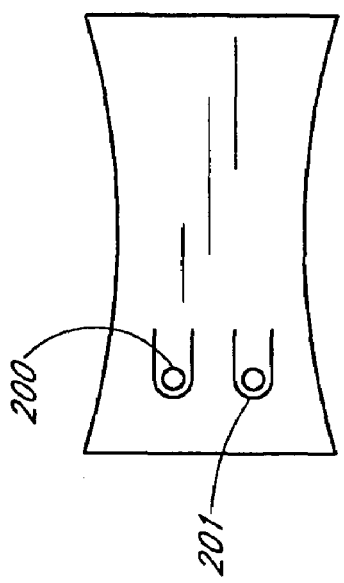
FIGS. 5 and 6 are top plan views of two different modifications of the base alone of the device of FIGS. 1 to 4.

Circular holes with radiused sides have been disclosed, as seen in FIG. 6, wherein like numerals refer to like parts of FIGS. 1 to 4, the holes for passage of the strands therethrough may include hole portions 200 extending through tabs or ears 201 which may be cut out of the support base and support plate or a single structure comprising both support base and support plate as disclosed below. The hole portions 200 communicate with aligned holes through the remaining portions of the base 14. The tabs 201 will thus flex slightly when the strands are pulled through the hole portions 200 and thereby exert a downward force through the strand on the connector once the strands are tightened around and/or over the connector. An upward force on the tabs forces the support base and plate to contour around the connector and thus prevents rolling of the device on the base.

Figure 7:
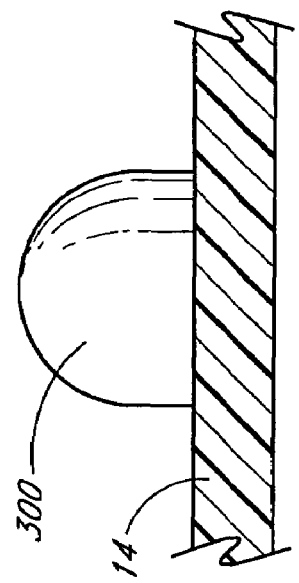
FIG. 7 is a perspective view of a portion of another embodiment of the base of FIG. 1.

In still another embodiment of the invention, as seen in FIG. 7 wherein like numerals refer to the embodiment of FIG. 1, base 14 may have hemispherically shaped protrusions, such as protrusions 300, extending upwardly therefrom instead of conically shaped protrusions. Also, as seen in FIG. 8, wherein like numerals refer to like parts of FIG. 1, tabs 400, 400' with holes 401, 401', respectively, therethrough, similar to tabs 201 and holes 200 in FIG. 6, may be provided on the upper surface of base 402. The area 403 is concave but raised slightly at the midpoint 404 thereof to provide a ramp for a connector or the like. That is, the area 403 may slope upwardly from one side 403' to midpoint 404, then slope downwardly from midpoint 404 to the other side 405'. In this embodiment, a single strand 405, otherwise identical to strands 16, 24, FIG. 9, may extend up through one hole 401, knotted on the underside of the lower support plate 33, as at knot 406, extend through hole 401 in the tab 400 as shown, then extends through hole 401' in post 400' and tied back upon itself, thus retaining a connector or the like (not shown).

The strands may be of silk or any flexible material that is substantially non-extendible about its long axis. The flexible beam 35 conforms to the shape of a connector mounted on the base and creates and maintains tension in the strands so as to keep any knots tight and pulls or presses the connector into the conforming surface preventing rolling. Also, beam 35 may be integral with plate 33 and base 32 with the hardness of the securement base 14 varying from the top to bottom thereof or of uniform hardness to allow both the cushioning/conforming effect of said base and the springlike character of said plate.

Although a particular embodiment of the invention is disclosed, variations thereof may occur to an artisan and the scope of the invention should only be limited by the scope of the appended claims.

The invention claimed is:

1. A securement device for a percutaneous sheath introducer or another medical article comprising:
   a pad having an adhesive surface on one side thereof adapted to adhere to the skin of a patient at least when exposed to the atmosphere;
   a peel-off backing sheet adhering to at least a portion of said pad and adapted to be peeled away from said pad;
   a securement base secured to said pad, said base being comprised of a first upper support base portion supported at least in part by a second lower support plate, said support plate being secured to said pad and including at least one biasing member, at least a portion of said biasing member being disposed below said first upper support base portion and having a generally fixed base and a deflectable beam section that flexes relative to said fixed base; and
   at least one elongated strand being coupled to said biasing member and having a free end, said free end being configured to be tied about a portion of said medical article and secured relative to said securement base.

2. The device of claim 1 wherein said base has one or more holes extending therethrough, and wherein said beam section is embedded in said second lower support plate, said strand extending through said beam section when inserted into the holes in said base.

3. The device of claim 2 wherein said base has at least 1 spaced hole.

4. The device of claim 2 wherein said one or more holes include at least one or more hole portion extending through said upper support base portion and at least one or more hole portion extending through said lower support plate, said hole portions being aligned to form said at least one or more holes through said base.

5. The device of claim 2 wherein said holes extending through said base include hole portions through tabs cut out of the upper surface of said base and attached at one end to the upper surface of said base and said hole portions communicating with hole portions through the remainder of said base.

6. The device of claim 1 wherein said base has a concave portion in substantially the middle thereof.

7. The device of claim 1 wherein said base has a first elongated end wall spaced from a second elongated end wall, and said end walls are interconnected by spaced side walls curving inwardly at generally the midpoint thereof.

8. The device of claim 7 wherein said base has a concave portion at generally the midpoint thereof extending from one of said side walls where said side wall curves inwardly to the other.

9. The device of claim 8 wherein one end of said concave portion is raised with respect to the other.

10. The base of claim 8 wherein one end of said base adjacent one of said end walls slopes inwardly toward the center, then downwardly toward the other end wall to form a center raised portion.

11. The device of claim 1 including a plurality of spaced protrusions upwardly extending from said base.

12. The device of claim 11 wherein said protrusions are conically shaped having a wide base portion at its connection to said base extending upwardly to a rounded tapered end.

13. The device of claim 12 wherein said protrusions vary in overall height.

14. The device of claim 1 wherein said base is of a polycarbonate material.

15. The device of claim 1 wherein said base is of a plastic material.

16. The device of claim 1 wherein said pad is of a fabric material overlaid by a hydrocolloid adhesive material.

17. The device of claim 1 wherein said at least one strand is of a silk material.

18. The device of claim 1 wherein said at least one strand is of flexible material.

19. The device of claim 1 wherein said at least one strand is of a flexible material substantially non-extendable along its long axis.

20. The device of claim 1 wherein said upper support base portion is of a polymeric material.

21. The device of claim 1 wherein said biasing member is embedded in said second lower support plate and conforms substantially to the configuration of said lower support plate and to said retained portion of said medical article disposed on said base, said strand extending about and under said biasing member.

22. The device of claim 21 wherein said biasing member creates and maintains tension on said at least one strand when said at least one strand is secured to said base.

23. The device of claim 22 wherein said base has one or more holes extending therethrough, and wherein said at least one strand is knotted in said at least one hole through said base.

24. The device of claim 23 wherein said at least one strand is glued to the underside of said second lower support plate.

25. The device of claim 1 wherein said biasing member is integral with said lower support plate and substantially conforms to the configuration of said lower support plate, said securement base varying in hardness from the top to bottom thereof, said strand extending about and under said biasing member.

26. The device of claim 1, wherein said at least one strand has one end glued at the bottom thereof to said base.

27. A securement device for a percutaneous sheath introducer or another medical article comprising:
   a pad having an adhesive surface on one side thereof adapted to adhere to the skin of a patient at least when exposed to the atmosphere;
   a peel-off backing sheet adhering to at least a portion of said pad and adapted to be peeled away from said pad;
   a securement base secured to said pad, said base being comprised of a first upper support portion and a second lower support portion, said first upper support portion being elastically deformable, and said second lower support portion being secured to said pad and being harder than said first upper support portion; and
   at least one elongated strand being coupled to said base and having a free end, said free end being configured to be tied about a portion of said medical article and secured relative to said securement base.

28. The device of claim 27 wherein said base has one or more holes extending therethrough, and wherein said at least one strand has one end knotted in said hole extending through said base at the bottom thereof.

29. The device of claim 27 wherein said at least one strand has one end glued at the bottom thereof to said base.

30. The device of claim 27 wherein said base has at least two holes, one of said holes extending through a tab on the upper surface of said base, the other of said holes being disposed in a post extending upwardly from said base spaced from said tab, said at least one strand extending upwardly through said one of said holes and knotted at the bottom of the hole through said base, then through the hole in said post where the free end of said strand is adapted to be tied to itself and about a connector on an upper surface of said base.

31. The device of claim 30 wherein a concave area is provided in the first upper support portion extending across said base, said concave area having a raised portion at generally the middle thereof.

32. The device of claim 30 including a plurality of protrusions extending upwardly from said base.

33. The device of claim 32 wherein said post extends upwardly from said base above said protrusions, said hole through said post being at the upper end thereof.

34. The device of claim 27 further comprising at least one biasing member, at least a portion of said biasing member being disposed below said first upper support portion and having a generally fixed base and a deflectable beam section that flexes relative to said fixed base.

35. The device of claim 27, wherein said securement base increases in hardness from the bottom to the top.

36. The device of claim 27, wherein said first upper support portion is comprised of a polymeric material that has a Shore A hardness of no greater than 35 A durometer.

37. The device of claim 27, wherein said second lower support portion produces compressive stresses within said first upper support portion that bear against said portion of said medical article when said medical article is secured to said securement base.

38. The device of claim 27, wherein said second lower support portion is comprised of a first material and the first upper support portion is comprised of a second material, and the second material is softer than the first material.

39. The device of claim 38, wherein said second material is a polymeric material.

40. The device of claim 38, wherein said first material is a polycarbonate.

41. A securement device for a percutaneous sheath introducer or other medical articles comprising:
   a pad having an adhesive surface on one side thereof adapted to adhere to the skin of a patient when exposed to the atmosphere;
   a peel off backing sheet adhering to at least a portion of said pad and adapted to expose said pad to the atmosphere when peeled away from said pad;
   a securement base fixedly secured to said pad, said base having at least two spaced holes extending therethrough, one of said holes extending through a tab on the upper surface of said base, the other of said holes being disposed in a post extending upwardly from said base spaced from said tab, said base being comprised of a first upper support base portion secured to a second lower support plate, said support plate being secured to said pad, wherein a concave area is provided in the upper support base portion extending across said base, said concave area having a raised portion at generally the middle thereof; and
   at least one flexible elongated strand having a free end one extending upwardly through said one of said holes and knotted at the bottom of the hole through said base, then through the hole in said post where the free end of said strand is adapted to be tied to itself and about a connector on the upper surface of said base.

42. A securement device for a percutaneous sheath introducer or other medical articles comprising:
   a pad having an adhesive surface on one side thereof adapted to adhere to the skin of a patient when exposed to the atmosphere;
   a peel off backing sheet adhering to at least a portion of said pad and adapted to expose said pad to the atmosphere when peeled away from said pad;
   a securement base fixedly secured to said pad, said base having at least two spaced holes extending therethrough and a plurality of protrusions extending upwardly from said base, one of said holes extending through a tab on the upper surface of said base, the other of said holes being disposed in a post extending upwardly from said base spaced from said tab, said base being comprised of a first upper support base portion secured to a second lower support plate, said support plate being secured to said pad; and
   at least one flexible elongated strand having a free end one extending upwardly through said one of said holes and knotted at the bottom of the hole through said base, then through the hole in said post where the free end of said strand is adapted to be tied to itself and about a connector on the upper surface of said base.

43. A securement device for a percutaneous sheath introducer or other medical articles comprising:
   a pad having an adhesive surface on one side thereof adapted to adhere to the skin of a patient when exposed to the atmosphere;
   a peel off backing sheet adhering to at least a portion of said pad and adapted to expose said pad to the atmosphere when peeled away from said pad;
   a securement base fixedly secured to said pad, said base having at least two spaced holes extending therethrough and a plurality of protrusions extending upwardly from said base, one of said holes extending through a tab on the upper surface of said base, the other of said holes being disposed in a post extending upwardly from said base spaced from said tab, said base being comprised of a first upper support base portion secured to a second lower support plate, said support plate being secured to said pad, wherein said post extends upwardly from said base above said protrusions, said hole through said post being at the upper end thereof; and
   at least one flexible elongated strand having a free end one extending upwardly through said one of said holes and knotted at the bottom of the hole through said base, then through the hole in said post where the free end of said strand is adapted to be tied to itself and about a connector on the upper surface of said base.

* * * * *